US00PP24967P3

(12) United States Plant Patent
Suphachadiwong

(10) Patent No.: US PP24,967 P3
(45) Date of Patent: Oct. 14, 2014

(54) *DENDROBIUM* PLANT NAMED 'SUDEN1201'

(50) Latin Name: ***Dendrobium* hybrid**
Varietal Denomination: Suden1201

(75) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 258 days.

(21) Appl. No.: 13/507,703

(22) Filed: Jul. 20, 2012

(65) Prior Publication Data

US 2014/0026270 P1 Jan. 23, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Dendrobium* cultivar named 'Suden1201' is disclosed, characterized by unique splash type flower coloration. The new variety is a *Dendrobium,* typically produced as an indoor ornamental plant.

1 Drawing Sheet

Latin name of the genus and species: *Dendrobium* hybrid. Variety denomination: 'Suden1201'.

BACKGROUND OF THE INVENTION

The new cultivar is the product of chance discovery. The new variety originated as a naturally occurring whole plant mutation of the unpatented proprietary variety referred to as 'FZ2OK×91 No. 1' variety of *Dendrobium* hybrid.

The new variety was discovered by the inventor, Thumrong Suphachadiwong, a citizen of Thailand, during August of 2008 in a commercial greenhouse belonging to the inventor in Chonburi, Thailand. After identifying the new variety as a potentially interesting selection, the inventor continued confidential testing and propagation of 'Suden1201', assessing stability of the unique characteristics of this variety.

Asexual reproduction of the new cultivar 'Suden1201' was first performed at a commercial laboratory belonging to the inventor in Chonburi, Thailand by tissue culture in March of 2009. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'Suden1201' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Suden1201.' These characteristics in combination distinguish 'Suden1201' as a new and distinct *Dendrobium* cultivar:

1. Unique splash type flower coloration.

PARENT COMPARISON

Plants of the new cultivar 'Suden1201' are similar to the parent, *Dendrobium* 'FZ2OK×91 No. 1' in most horticultural characteristics. The new variety, however, produces flowers with splash type coloration, whereas 'FZ2OK×91 No. 1' produces flowers that are of solid coloration.

COMMERCIAL COMPARISON

'Suden1201' is similar to the unpatented commercial variety *Dendrobium* 'Burana Splash' in most horticultural characteristics. The new variety, however, produces darker purple colored flowers with lateral lobes of the flower touching, whereas 'Burana Splash' produces a lighter purple colored flower with open lateral lobes. The apical lobe of 'Sudan1201' is narrower and smaller than that of 'Burana Splash'. 'Sudan1201' produces a flower heart of a significantly different color than the flower heart of 'Burana Splash'.

BRIEF DESCRIPTION OF THE PHOTOGRAPH

The accompanying photograph in FIG. 1 illustrates in full color a typical plant of 'Suden1201' grown in a commercial greenhouse in Chonburi, Thailand. This plant is approximately 1 year old, shown planted in a 10.5 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Suden1201' plants grown in a greenhouse in Chonburi, Thailand. Temperatures ranged from 26° C. to 30° C. day. From 26° C. to 30° C. night. No artificial light, photoperiodic or chemical treatments were given to the plants. Measurements and numerical values represent averages of typical plant types.

Botanical classification: *Dendrobium* hybrid 'Suden1201'.

PROPAGATION

Type of propagation typically used: Tissue culture.

Time to produce a rooted cutting/liner: Tissue culture production takes 18 months. After deflasking it takes another 9 to 12 months to get a well-rooted plant under average temperatures ranging between 26° C. and 30° C.

Root description:

*Root color.*—Near RHS Yellow-White 158A.

*Average diameter.*—Average: 2 mm.

*Average length.*—Average: 11 cm.

PLANT

Growth habit: Sympodial, upright.

Height from top of soil line to top of foliage: 28.0 cm.

Height from top of soil line to top of flowers: 48.0 cm.

Plant spread: 30.8 cm.

Normal pot size: 10.5 cm circular pot.

Growth rate: Moderate.

Number of leaves per plant: Average: 12.

Plant stem:

*Length.*—Approximately 17.6 cm.

*Diameter.*—Approximately 1.8 cm.

*Aspect.*—Approximately 90° angle to soil surface.

*Strength.*—Strong.

*Texture.*—Smooth, dull, axially ribbed.

*Color.*—Near RHS Yellow-Green 144A and 144B.

FOLIAGE

Leaf:

*Arrangement.*—Distichous.

*Average length.*—Approximately 12.1 cm.

*Average width.*—Approximately 4.1 cm.

*Shape of blade.*—Ovate.

*Aspect.*—Leaves in an average angle of 30° to main stem (0°=vertical), curved, tip pointed downward in an average angle of −20° (0°=horizontal).

*Apex.*—Acute.

*Base.*—Decurrent. Sheath length: Average 0.4 cm. Sheath width: Average 0.3 cm. Sheath color: Near RHS Green 143A and 143B.

*Margin.*—Entire.

*Texture of top surface.*—Smooth, moderately glossy.

*Texture of bottom surface.*—Smooth, dull.

*Durability to physical stress.*—High.

*Color.*—Young foliage upper side: Near RHS Yellow-Green 146A. Young foliage under side: Near RHS Yellow-Green 146B. Mature foliage upper side: Near RHS Green N137B. Mature foliage under side: Near RHS Yellow-Green 147B.

*Venation.*—Type: Parallel. Venation coloration: Upper Surface: Near RHS Green N137B. Lower Surface: Near RHS Yellow-Green 144A Petiole: No petioles present. .

FLOWERING CHARACTERISTICS

General description:

*Flower bud.*—Rate of opening: Approximately 30 days from first sight. Length: Approximately 2.8 cm. Diameter: Approximately 1.1 cm. Shape: Oblong, curved. Color: Upper side near Purple N77B, lower side near RHS Yellow-Green 145C tip near Yellow-Green 146B.

*Peduncle.*—Length: Approximately 39.0 cm. Diameter: Approximately 0.2 cm. Aspect: Approximately 0° angle to rosette. Strength: Strong. Texture: Smooth, very slightly glossy. Color: Near RHS Yellow-Green 144B, tinged in between RHS 152A and N200A on the uppermost side, with most light exposure.

INFLORESCENCE

Flowers per stem: Average: 10.

Inflorescence arrangement: Simple raceme.

Inflorescence height: Approximately 30.0 cm (from lowest pedicel to top of inflorescence).

Inflorescence width: Approximately 11.5 cm.

INDIVIDUAL FLOWERS

*Flower type.*—Single, orchidaceous (zygomorphic), typical for *Dendrobium.*

*Rate of opening.*—After the first flower has opened, it takes approximately four weeks before the top flower opens.

*Shape.*—Orchidaceous (zygomorphic), typical for *Dendrobium,* with three sepals, two lateral petals and a labellum (third petal).

*Height.*—Approximately 5.0 cm, excluding sheath.

*Diameter.*—Approximately 5.8 cm.

*Depth.*—Approximately 3.1 cm.

*Fragrance.*—No fragrance.

*Persistent?.*—Non-persistent.

*Quantity of petals.*—Average: 3 (two lateral petals and a labellum (third petal)). Only the two lateral petals are described here as such.

Petals:

*Arrangement.*—Oppositely placed on each side of the column.

*Length.*—Approximately 3.8 cm.

*Width.*—Approximately 3.2 cm.

*Shape.*—Reniform to orbicular.

*Apex.*—Rounded.

*Base.*—Broad cuneate.

*Margin.*—Entire.

*Appearance.*—Dull, moderately velvety.

*Texture.*—Upper forward surface: smooth, moderately velvety.

*Texture.*—Lower back surface: smooth, slightly velvety.

*Color.*—When opening, forward surface: Near RHS Purple-Violet N80A, margin near the top irregularly variegated RHS Purple 76A and White N155D. When opening, back surface: In between RHS Purple-Violet N80A and N81B, margin near the top irregularly variegated RHS Purple 76A and White N155D. Fully Opened, forward surface: In between near RHS Purple N78A and Violet-Purple N80A, but slightly more reddish (not on R.H.S.-Colour Chart). Margin near the top irregularly variegated RHS Purple 76A and White N155D. Fully Opened, back surface: Near RHS Purple-Violet N80A, margin near the top irregularly variegated RHS 76A and N155D. Fading, forward surface: Not fading (colors same as "Fully Opened"). Fading, back surface: Near RHS Purple-Violet N81B, margin near the top irregularly variegated RHS 76A and N155C.

*Color venation fully opened, forward surface.*—Near RHS Red-Purple N71A.

*Color venation fully opened, back surface.*—Near RHS Violet-Purple N80A.

Labellum:

*Shape.*—Deltoid, strongly involute.

*Length.*—Approximately 3.1 cm.

*Width.*—Approximately 1.6 cm (when "unfolded open" approximately 3.7 cm).

*Texture.*—Smooth, moderately velvety.

*Appearance.*—Dull, moderately velvety.

*Tip.*—Abruptly acute.

*Base.*—Broad cuneate.

*Color.*—When opening, forward surface: Near RHS Purple N79C, margins and top irregularly variegated RHS Purple 76A and White N155D, base near RHS Yellow-Green 150D. When opening, back surface: Near RHS Purple N78A, margins and top irregularly variegated RHS Purple 76A and N155D, base near RHS Green-White 157A. Fully Opened, forward surface: Near RHS Purple N79C, margins and top irregularly variegated RHS Purple 76A and White N155D, base near RHS Yellow-Green 150D. Fully Opened, back surface: Near RHS Purple N78A, margins and top irregularly variegated RHS Purple 76A and White N155D, base near RHS Green-White 157A. Fading, forward surface: Near RHS Purple N78A to Purple N80A, margins and top irregularly variegated RHS 76D and NN155C, base near 145C to RHS 150D. Fading, back surface: Near RHS Purple N78A, margins and top irregularly variegated RHS Purple 76A and White N155C, base near RHS 150D.

*Color venation fully opened, forward surface.*—No venation visible.

*Color venation fully opened, back surface.*—No venation visible.

*Margin.*—Entire.

*Callosites.*—Dimensions: Average: 0.2 cm long and 0.1 cm wide. Location: At the base of the labellum, colored near RHS Yellow-Green 150D.

Sepals:

*Quantity.*—Average: 3.

*Appearance.*—Dull, moderately velvety.

*Length.*—Approximately 3.3 cm.

*Width.*—Approximately 1.7 cm.

*Shape.*—Ovate.

*Apex.*—Acute.

*Base.*—Broad cuneate.

*Margin.*—Entire.

*Texture.*—Smooth, moderately velvety.

*Color.*—Forward surface: Between RHS Purple N78A to N78B, Striped, margined and top irregularly variegated RHS Purple 76B and White N155D, base near RHS Green-White 157A. Back surface: Near RHS Purple 77B, margins variegated RHS White N155D, base near RHS Greyed-White 156C.

Pedicels:

*Length.*—Approximately 2.9 cm.

*Diameter.*—Approximately 0.2 cm.

*Angle.*—About 45° to 90° angle to peduncle.

*Strength.*—Moderately strong.

*Texture.*—Smooth, slightly glossy.

*Color.*—Upper side near RHS Greyed-Red 182B, under side near RHS Yellow-Green 146D.

REPRODUCTIVE ORGANS

Stamens, style and stigma fused into column?: Yes.

Column length: Average: 1.4 cm.

Column diameter: Average: 0.7 mm.

Column color: Near RHS Green-White 157A.

Ovary:

*Position.*—Superior, placed directly above stigma.

*Diameter.*—Average: 0.6 cm.

*Color.*—Near RHS Green-White 157B.

Stigma:

*Shape.*—Concave, circular.

*Color.*—Near RHS Yellow-Green 147D.

*Dimensions.*—Average: 0.3 cm wide and high.

Pollinia:

*Color.*—Near RHS Yellow 13A.

*Dimensions.*—Average: 0.2 cm long and 0.1 cm wide.

*Quantity.*—2.

OTHER CHARACTERISTICS

Disease resistance: High.

Drought tolerance and cold tolerance: Normal.

Fruit/seed production: No fruits/seeds detected to date.

Any other characteristics: No.

What is claimed is:

1. A new and distinct cultivar of *Dendrobium* plant named 'Suden1201' as herein illustrated and described.

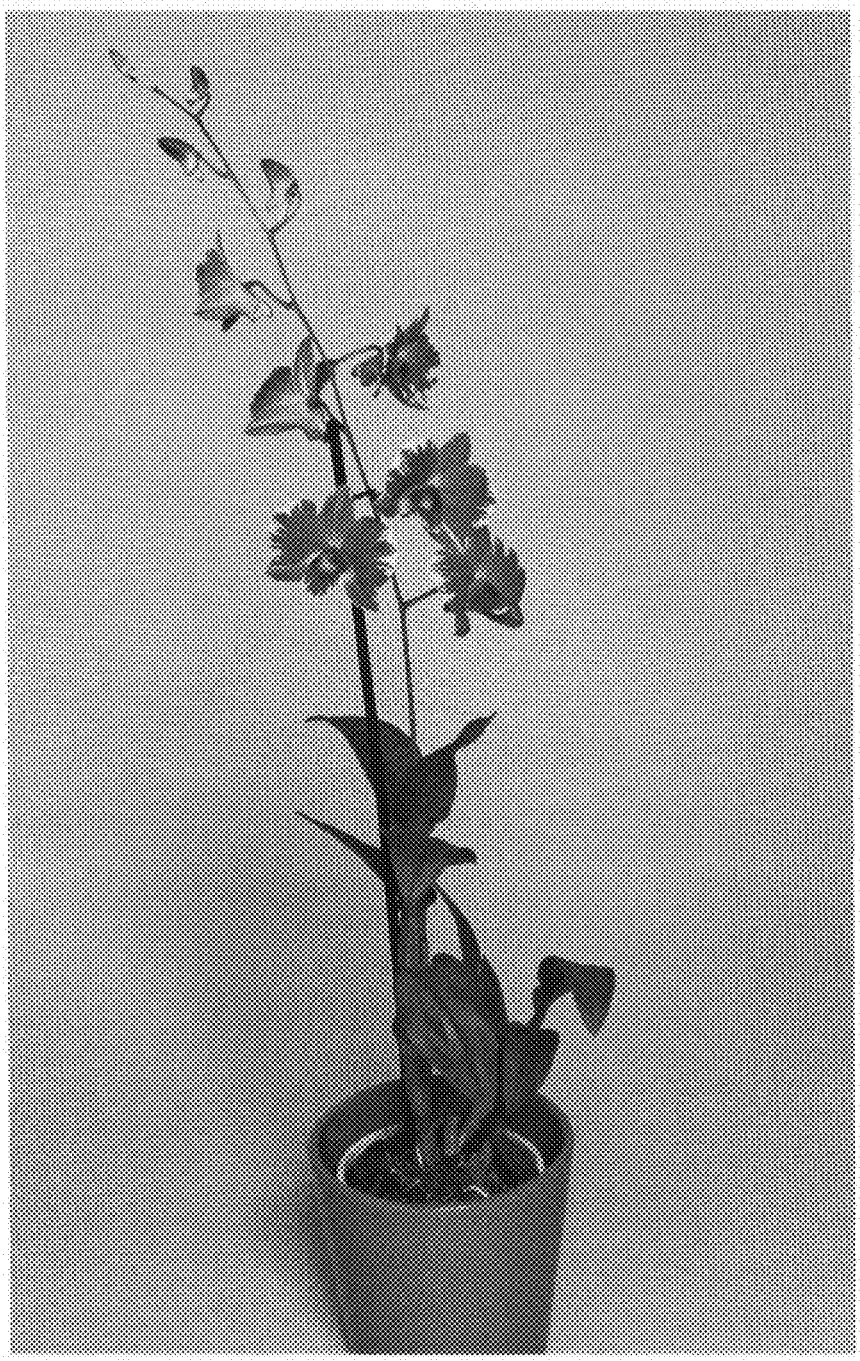

* * * * *